United States Patent [19]

Baxter

[11] Patent Number: 4,505,799
[45] Date of Patent: Mar. 19, 1985

[54] ISFET SENSOR AND METHOD OF MANUFACTURE

[75] Inventor: Ronald D. Baxter, Furlong, Pa.

[73] Assignee: General Signal Corporation, Stamford, Conn.

[21] Appl. No.: 631,507

[22] Filed: Jul. 16, 1984

Related U.S. Application Data

[63] Continuation of Ser. No. 559,513, Dec. 8, 1983, abandoned.

[51] Int. Cl.$^3$ ...................... H01L 21/60; G01N 27/30
[52] U.S. Cl. ...................... 204/416; 29/571; 29/576 W; 29/580; 29/589; 29/591; 204/433; 357/25
[58] Field of Search ........................ 357/25; 324/71.5; 204/416, 418, 419, 420, 433; 29/571, 576 W, 580, 589, 591

[56] References Cited

PUBLICATIONS

L. A. D'Asaro et al., IEEE Trans., vol. ED-25, No. 10, pp. 1218-1221, Oct. 1978.
D. J. Ehrlich et al., IEEE Trans. On Components, Hybrids & Manufac. Tech., vol. CHMT-5, No. 4, pp. 520-521, (1982).
Roy A. Colclaser, "Microelectronics: Processing and Device Design", p. 198, (1980).
Jay N. Zemel, Research/Development, vol. 28, No. 4, pp. 38, 39, 41, 42, 44, (1977).
P. W. Cheung et al., "Theory, Design and Biomedical Applications of Solid State Sensors, pp. 91-115, (1978).
J. C. M. Huang et al., IEEE Proc. IEDM Meeting, Dec. 13-15, 1982, Pub. Jan.-Feb. 1983.
Ching-Chang Wen, Graduate Dissertation, U. of Pa., pp. 19 and 36, (1979).
T. Matsuo et al., Sensors and Actuators, 1, pp. 77-96, (1981).
P. Bergveld et al., Sensors and Actuators, 1, pp. 5-15, (1981).
A. Reisman et al., J. Electrochem. Soc., Solid State Science & Tech., pp. 1406-1415, (1979).
H. S. Gamble et al., J. Electrochem. Soc., pp. 990-992, Apr. 1980.
A. Bohg, J. Electrochem. Soc., Electrochem. Technol., pp. 401-402, Feb. 1971.
T. O. Sedgwick et al., J. Electrochem. Soc., Solid State Science & Technol., pp. 1769-1771, Dec. 1972.

Primary Examiner—G. L. Kaplan
Attorney, Agent, or Firm—W. G. Miller, Jr.; Harold Huberfeld

[57] ABSTRACT

There is provided an ISFET structure and a method for manufacturing that structure such that external electrical contact to the P+ source and drain regions is made through individual holes etched from the back to the source and drain regions with sidewall isolation being provided in the holes and metallization covering the surface of said sidewalls and extending to contact pads on the back of the ISFET.

14 Claims, 14 Drawing Figures

ISFET SENSOR AND METHOD OF MANUFACTURE

This is a continuation of application Ser. No. 559,513 filed on Dec. 8, 1983 and now abandoned.

BACKGROUND OF THE INVENTION

This invention relates to chemical or electrochemical sensors based on Si FET technology and particularly relates to the construction of such devices for the measurement of hydrogen ions (pH) and other ion activity in solution. Such devices are known as ISFET's (ion selective field-effect transistors) and are similar to conventional insulated gate FET's except that the metal gate electrode is removed and the gate region is covered by a suitable insulator film. This insulating layer acts as the ion selective, sensitive membrane.

In its use as a pH sensor, the ISFET must be immersed in an electrolyte which, from the standpoint of the normal electrical connections made to the front side, is a very hostile environment. It is, therefore, desirable to design the ISFET so as to minimize contact between the electrical circuitry and the electrolyte solution so that the integrity, stability, and reliability of the device is maintained.

In the past many attempts have been made to achieve the desired isolation between the environment to which the ISFET is exposed and its associated electrical circuitry. These attempts have generally been in biomedical applications and have involved approaches such as locating the metallized source and drain bonding pads several millimeters from the gate region with electrical access being accomplished through diffused silicon conductors. In those devices the metallized surface forming the pads is protected from the environment by the use of epoxies or silicone rubber. This approach typically results in a long, slender probe which may be 150 microns thick by 500 microns wide by 600 microns long. While such probes may be suited for medical applications they have disadvantages in laboratory and industrial applications, for they present higher lead impedances due to the relatively long path of the conductors leading from the gate region. Also, they do not have the durability and reliability necessary to operate under the more extreme environments encountered outside the medical field.

As indicated above, the prior art devices typically use contacts on the front side (the chemically or electrochemically responsive side) of the ISFET. Thus, protection is required for the circuit leads or circuit elements to isolate them from the environment. In some cases this protection has been attempted by providing contact from the back of the device. This has been done, for example, by making contact with the source and drain by way of holes which have been laser machined all the way through the device or by migrating aluminum through the device. These methods all have the disadvantage of producing either a disrupted front surface or a region which is not mechanically strong. In this connection, it should be pointed out that a planar front surface is desirable in order to avoid susceptibility to contamination which can cause a fouling of the gate membrane.

It is an object of this invention to provide a method and means for providing an ISFET probe having protected contacts while maintaining a planar front surface which is mechanically strong. More particularly, it is an object of this invention to provide a method for producing back contacts for the source and drain regions of an ISFET probe which introduce no mechanical or electrical problems affecting the stability and durability of the probe.

SUMMARY OF THE INVENTION

There is provided an ISFET structure such that external electrical contact to the source and drain regions is made through individual holes etched from the back up to the source and drain regions with sidewall isolation being provided in the holes and metallization covering the surface of said sidewalls and extending to contact pads on the back of the ISFET. This ISFET is manufactured by using a silicon substrate having a crystallographic structure with a (100) orientation. An orientation dependent etch is used to etch the holes to the source and drain regions where the presence of an etch stop halts the etching process. A doped region is then created in the sidewalls of the holes to provide the isolation from the substrate and the metallization is then laid on the sidewalls to provide the external contacts.

DESCRIPTION OF THE PREFERRED EMBODIMENT

Figure 1:
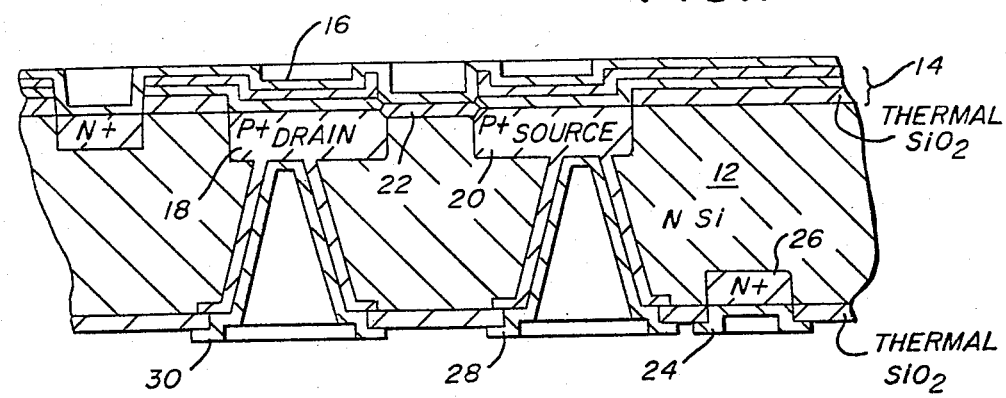
FIG. 1 is a cross section of an ISFET made in accordance with this invention.

There is shown in FIG. 1 a cross-section of an ISFET chip having the desired structure as obtained when manufactured in accordance with this invention. The substrate 12 is a silicon crystal having an orientation of (100), shown as N-Si. On the front side the substrate is successively coated with a number of oxides 14, more fully described later, and an ion sensitive membrane 16, such as silicon nitride or aluminum oxide. The substrate is doped to have a P+ drain region 18 and a P+ source region 20. In the area between the source and drain there is a window in the field oxide where a gate oxide 22 has been grown under the ion sensitive membrane. On the back side of the substrate 12 there is a field oxide coating which is windowed to provide the substrate contact 24 to an N+ region 26. Other windows are provided for the source contact 28 and the drain contact 30. These two contacts are made through holes etched in the back of the ISFET so as to form the pyramidal shaped holes shown in FIG. 1. The sidewalls of these holes are provided with an isolating P+ region for isolating the substrate, as shown in FIG. 1. Over the isolating P+ region of the sidewalls a metallization is deposited to provide the electrical contact from the back of the ISFET to both the source and drain. This metallization is carried from the sidewalls to the back to provide contact areas or pads for wire bonding the circuit leads necessary to incorporate the ISFET chip into a probe.

The construction of the ISFET of this invention generally follows standard long-channel FET technology with the exception of the means provided for making electrical connection to the source and drain region. For these connections, the present invention is utilized to avoid the problems pointed out above. Thus, the electrical contacts are provided in such a way that the front surface of the ISFET is not disturbed or weakened. As will be fully described in the subsequent description detailing the method of manufacturing the ISFET of this invention, the etching of the via holes from the back for the source and drain contacts is stopped at the source and drain boundaries by an etch stop. A preferred method of performing this etch stopping action has been found to be by dropping the source and drain regions to have a high concentration of boron. In this connection the inventor has used a boron concentration greater than $5 \times 10^{19} cm^{-3}$ with the etchant ethylenediamine-pyrocatechol-water.

The preferred process for manufacturing an ISFET in accordance with this invention is set forth below.

1. Start with an N type wafer of silicon with a crystallographic orientation (100), a resistivity of about 3 ohm-cms, a diameter of 2 inches, and a thickness of 6 mils (polished both sides).

Figure 2A:
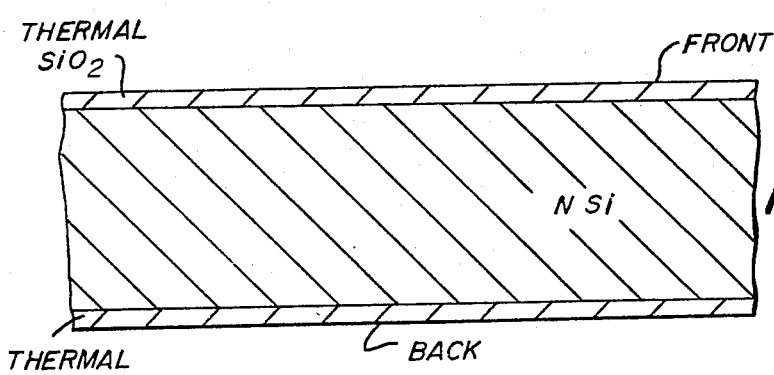
FIGS. 2A through 2J are cross section drawings showing the steps in the construction of the ISFET of this invention.

2. Grow a field oxide in wet oxygen on both back and front to a thickness of 7,000 Å, as shown in FIG. 2A.

3. Etch holes all the way through for registration purposes.

Figure 2B:
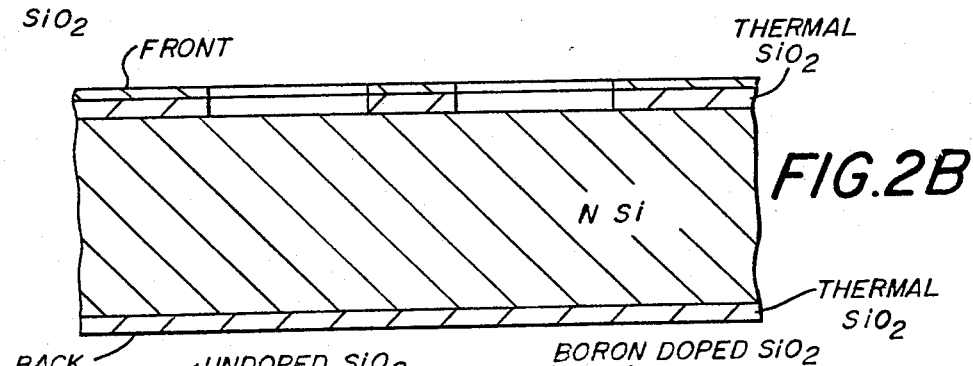

4. Open windows on the front in the field oxide for the source-drain diffusion step by coating with photoresist except in the areas to be opened and then etching those areas, as shown in FIG. 2B.

Figure 2C:
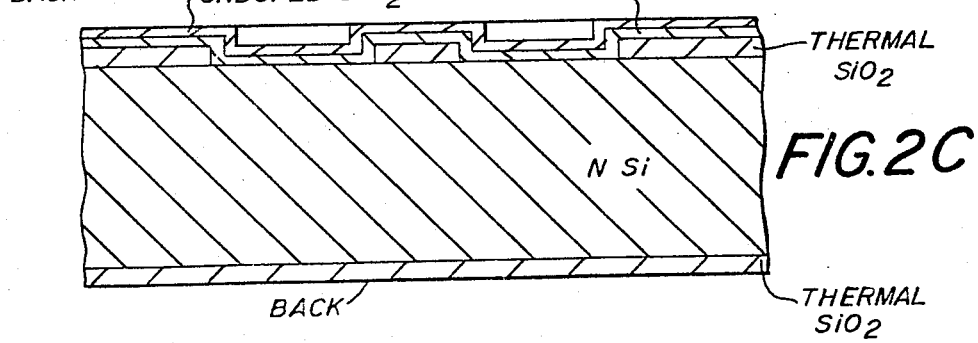

5. Deposit boron doped silicon dioxide by chemical vapor deposition using silane and oxygen with $B_2H_6$ as a dopant and a source of boron. Deposit the boron doped silicon dioxide to a thickness of 2500 Å and cover with another 2500 Å of undoped silicon dioxide, as shown in FIG. 2C. In the chemical vapor deposition process use 10 percent dibromane to total hydrides.

Figure 2D:
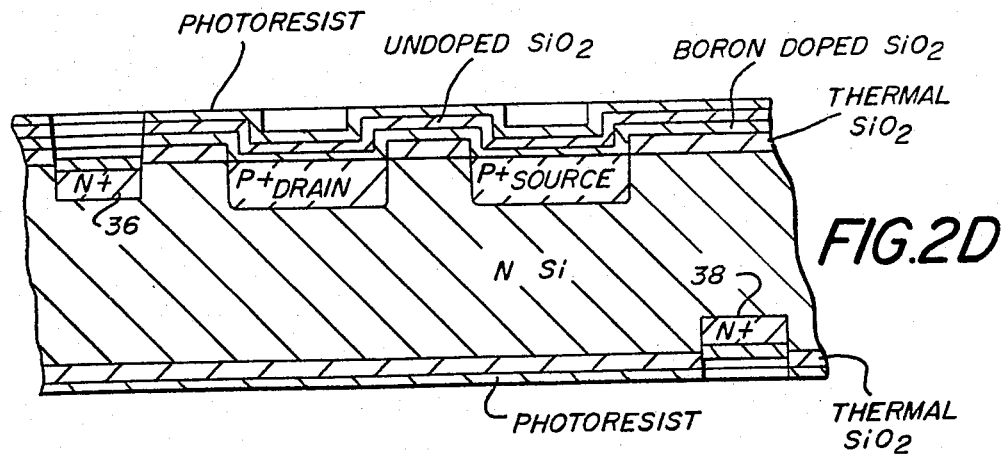

6. The drive step of the boron diffusion process is carried out at 1175° C. for 90 minutes, which gives a depth of 4–6μ for the resulting P+ source and drain regions, as shown in FIG. 2D.

7. Etch other windows on the front for the channel stop using a photoresist and an etch to provide for the production of the N+ region 36 of FIG. 2D.

8. Etch another window on the back for the substrate contact which will be provided by the generation of the N+ region 38 of FIG. 2D.

9. Do a phosphorous diffusion on both front and back using solid sources at 950° C. for 30 minutes. This deposition is followed by a 1100° C. drive for 30 minutes. The result is the production of the N+ regions 36 and 38 of FIG. 2D.

Figure 2E:
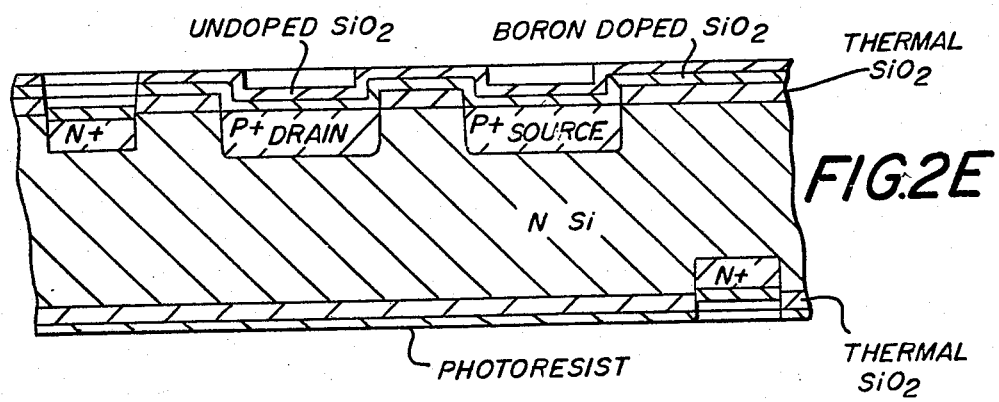

10. Open windows in the oxide on the back opposite the source and drain regions as shown in FIG. 2E using photoresist to cover the part that is not to be etched.

Figure 2F:
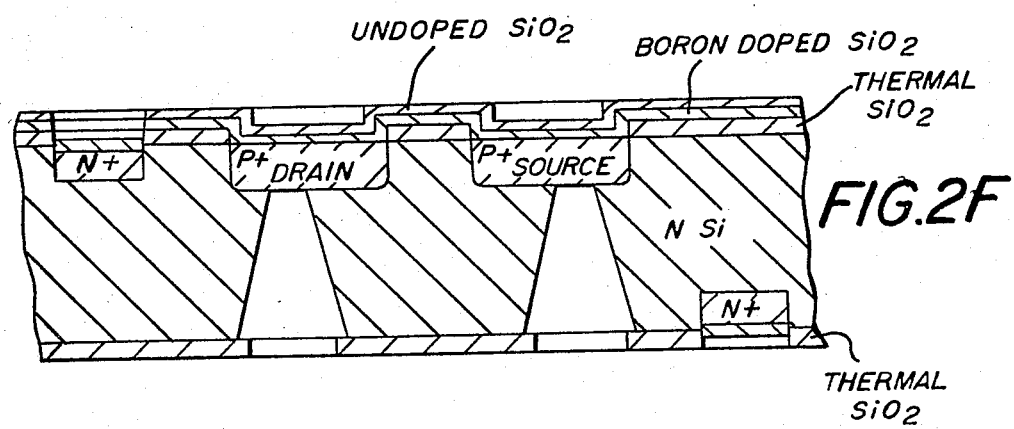

11. Etch holes in the silicon substrate to provide access from the back up to the source and drain regions. Use Ethylenediamine-pyrocatechol-water as the etchant. This etch will terminate at the source and drain regions because of the boron concentration in the source and drain. This etching process produces areas of oxide which overhang the sidewalls, as shown in FIG. 2F.

Figure 2G:
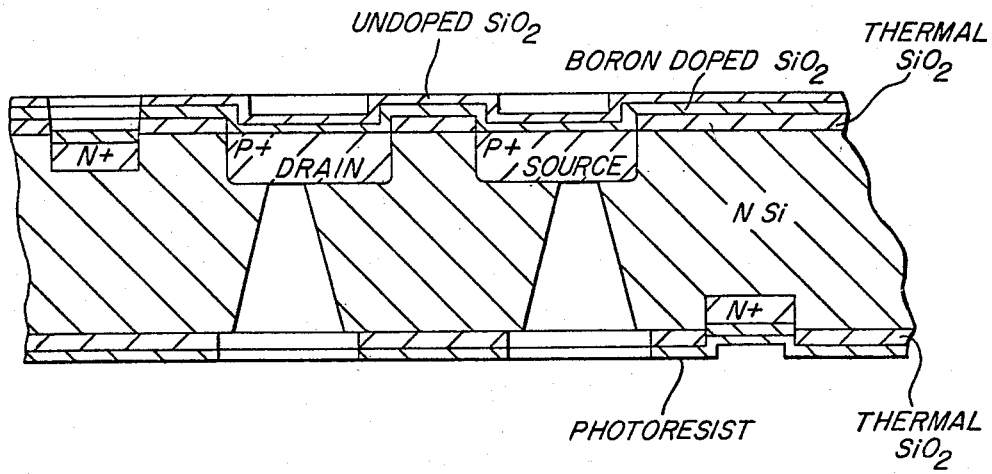

12. The overhanging areas are removed by etching, as shown in FIG. 2G.

Figure 2H:
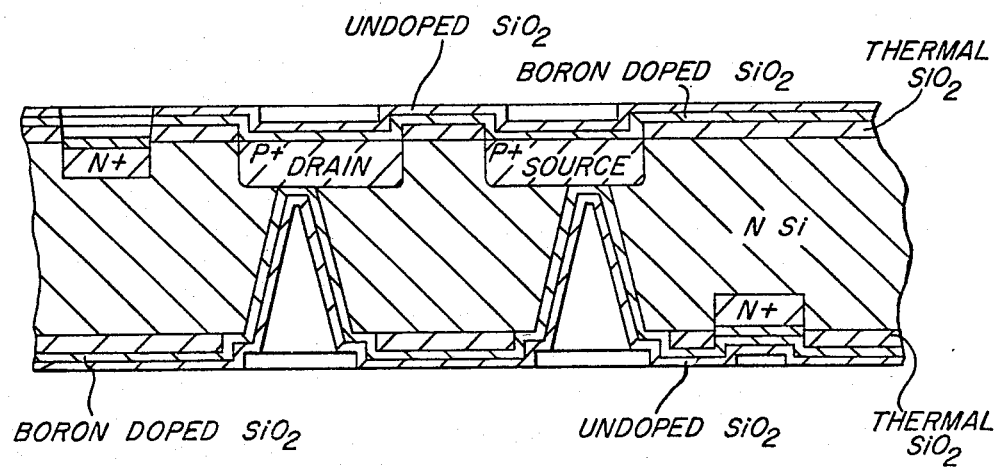

13. Produce the P+ regions in the sidewalls of the holes to isolate the N type silicon substrate from the contacts to be formed. Thus, source and drain regions are formed in the sidewalls of the etched holes. The process for doing this is the same as for producing the source and drain regions. Thus, the boron doped silicon dioxide is layed on the back and covered by an undoped silicon dioxide, as shown in FIG. 2H.

14. Drive the diffusion into the sidewalls at 1100° C. for 30 minutes.

Figure 2I:
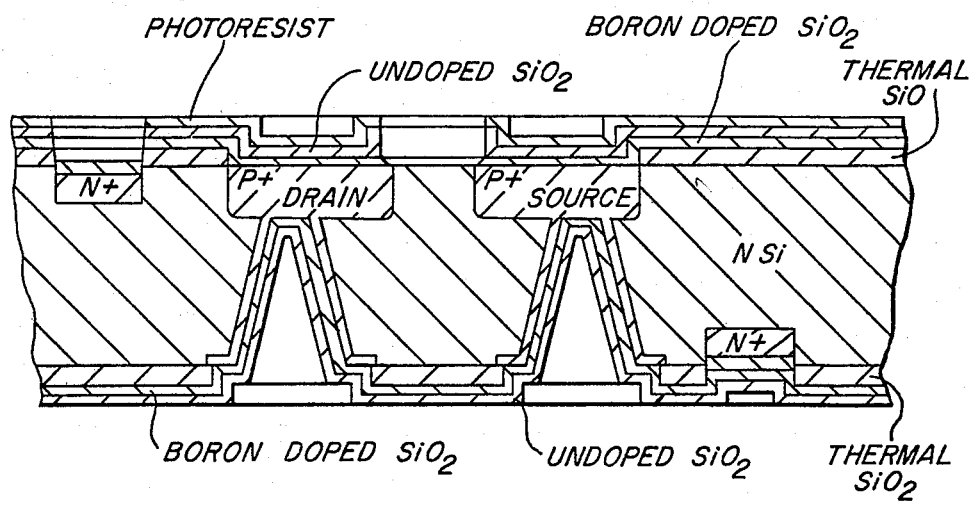

15. Open a window in the oxide on the front by etching, as shown in FIG. 2I, for providing the gate.

Figure 2J:
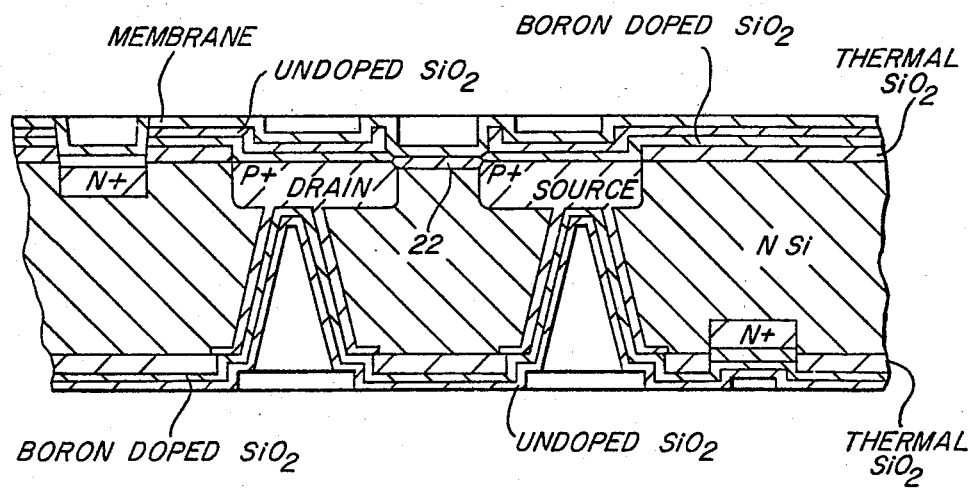

16. Grow a dry gate oxide 22, as shown in FIG. 2J.

17. Deposit an ion sensitive membrane over the front, as shown in FIG. 2J. This membrane may, for example, be silicon nitride or aluminum oxide where the ISFET is to be used to make pH measurements.

18. Open the contact regions on the back by etching away the various oxide layers.

19. Metallize the contact areas including the sidewalls of the holes and associated areas on the back as contact pads for connection of the external circuitry to the source, drain and substrate regions, as shown in FIG. 1.

Figure 3:
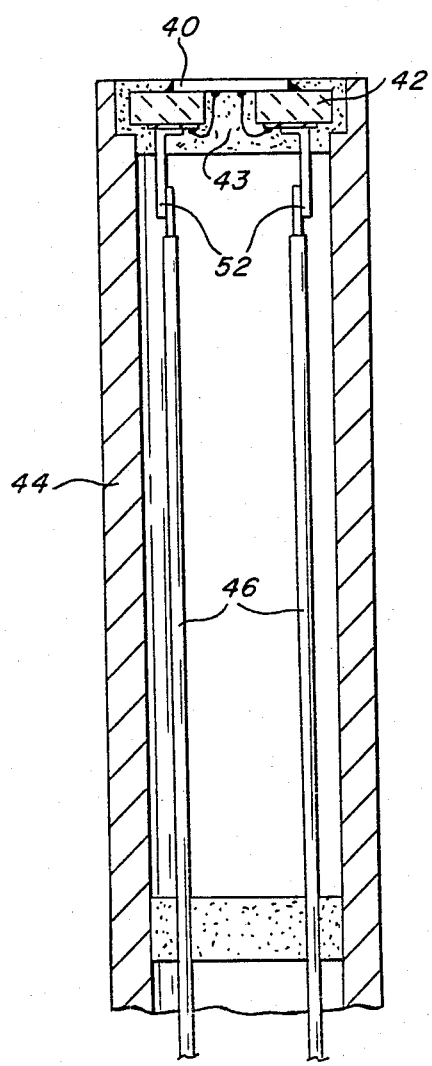
FIG. 3 is a cross section of a probe holding the ISFET of the invention.

For the purpose of using an ISFET manufactured in accordance with the above process, it is necessary to mount the ISFET chip in a holder or probe assembly. This probe may have the construction shown in FIG. 3, where the chip is shown mounted on a header 42. The header with its mounted chip is potted with epoxy or silicone 43 in the end of the probe body 44 with the insulated leads 46 extending along the length of the probe body with epoxy used in other areas to seal and support. The probe body may be made from a spin cast epoxy or other suitable material depending on the uses of the probe.

Figure 4:
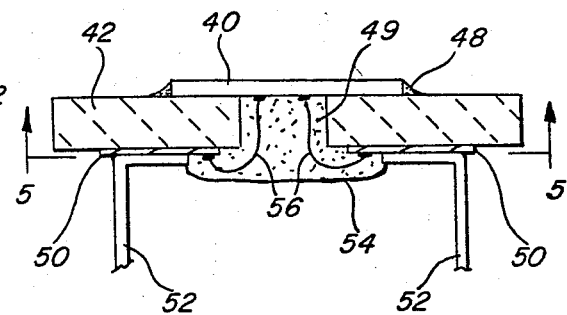
FIG. 4 is a cross section of a header assembly for holding the ISFET of the invention in a probe.

The mounting of the ISFET chip on the header is shown in detail in FIG. 4. The ISFET chip is epoxied to the top of the header by placing epoxy 48 around the edges of the chip. The header is a circular piece of aluminum oxide or a pyrex disc having a square hole 49 in the center and areas of thick film metallization 50 on the back to provide a place for bonding the lead outs 52 which will be soldered to the leads 46. The epoxy 54 fills the hole in the header and secures the electrical leads 56 to provide a rugged structure for the probe.

Figure 5:
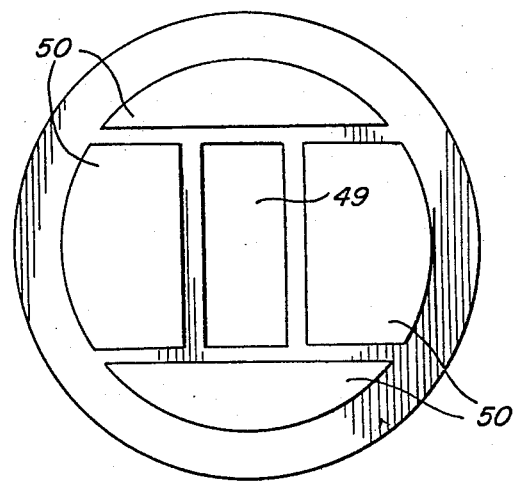
FIG. 5 is a bottom view of the header assembly of FIG. 4.

FIG. 5 shows a bottom view of the header itself with the areas of metallization 50 shown.

If desired the epoxy 48 holding the ISFET chip to the header can be replaced with an anodic bond if the header is made of pyrex.

What is claimed is:

1. In an ISFET with N-type silicon substrate having a crystal orientation of (100) which is doped to provide P+ source and drain regions, an external electrical source and drain contact structure, comprising:
   individual holes etched by an orientation dependent etch from the back of the ISFET to the source and drain regions,
   doped P+ regions in the sidewalls of said holes to provide electrical isolation of the surface of said sidewalls from said substrate, and
   a metallized surface deposited on the sidewalls of the holes and extending to separate associated contact areas on the back.

2. A method of providing electrical contact to a P+ source region and P+ drain region of an ISFET having an N-type silicon substrate with a crystallographic orientation of (100), comprising the steps of:
   providing an etch stopping characteristic to the source and drain regions, etching with an orientation dependent etch individual holes from the back of the substrate up to the source and drain regions, producing a P+ isolation region in the sidewalls of said holes, and metallizing over said sidewalls and onto the back to provide the electrical contacts for said source and drain regions on the back of said ISFET.

3. The method of claim 2 in which the source and drain regions are provided with an etch stopping characteristic by producing them through diffusion of boron into the silicon substrate so that said regions have a boron concentration sufficient to provide the necessary etch stopping characteristic.

4. The method of claim 3 in which boron concentrations greater than $5 \times 10^{19} cm^{-3}$ are produced in the source and drain regions by diffusion from a boron doped silicon dioxide layer.

5. The method of claim 4 in which the diffusion is driven at 1175° C. for 90 minutes.

6. The method of claim 4 in which the etchant used to etch the holes is Ethylenediamine-pyrocatechol-water.

7. An ISFET probe, comprising:
an ISFET chip having,
an N-type silicon substrate with a (100) crystallographic orientation,
P+ source and drain regions,
individual holes etched by an orientation dependent etch from the back of the ISFET up to the source and drain regions,
P+ regions in the sidewalls of said holes to provide electrical isolation of the surface of said sidewalls from said substrate, and
a metallized surface deposited on the sidewalls of the holes and extending to separate associated contact areas on the back,
a tubular probe body,
a circular header having the ISFET chip mounted on one side thereof and having thick film metallization in separated regions on the other side,
lead outs bonded to said metallized areas,
wire connections between said metallized areas on said header and said contact areas on the back of said chip,
insulated leadwire connected to said lead outs and extending the length of the probe body,
said header and the mounted ISFET chip with associated lead outs and wire connections being potted in the end of said probe body, and
means for supporting the insulated leads in said body.

8. An ISFET pH sensor comprising:
an N-type silicon substrate having a (100) crystallographic structure,
a doped P+ source region in the front of said substrate,
a doped P+ drain region in the front of said substrate,
a doped N+ channel stop region in the front of said substrate,
a doped N+ substrate contact region in the back of said substrate,
a gate oxide grown on the front of said substrate,
a field oxide coating on the front surface of said substrate with an opening in the area in front of the gate oxide,
a pH sensitive membrane covering the field oxide coating and the gate region,
individual holes etched from the back of said substrate up to the source and drain regions by on orientation dependent etch,
a doped P+ region in the sidewalls of said holes to isolate said substrate,
a metallized coating covering the surface of said holes and contacting the respective source and drain regions, said coating extending to the back surface of said substrate to form contact pads thereon, and
a metallized coating covering the substrate contact region and being in contact therewith.

9. An ISFET as set forth in claim 8 in which the source and drain regions have a boron concentration greater than $5 \times 10^{19} cm^{-3}$.

10. In an ISFET having a silicon substrate with a crystal orientation of (100) which is doped to provide source and drain regions, an external electrical source and drain contact structure, comprising:
individual holes etched by an orientation dependent etch from the back of the ISFET to the source and drain regions,
doped regions in the sidewalls of said holes to provide electrical isolation of the surface of said sidewalls from said substrate, and
a metallized surface deposited on the sidewalls of the holes and extending to separate associated contact areas on the back.

11. A method of providing electrical contact to a source region and drain region of an ISFET having a silicon substrate with a crystallographic orientation of (100), comprising the steps of:
providing an etch stopping characteristic to the source and drain regions,
etching with an orientation dependent etch individual holes from the back of the substrate up to the source and drain regions,
producing an isolation region in the sidewalls of said holes, and
metallizing over said sidewalls and onto the back to provide the electrical contacts for said source and drain regions on the back of said ISFET.

12. In an ISFET having a silicon substrate with a crystal orientation of (100) which is doped to an opposite conductivity type from said substrate to provide source and drain regions, an external electrical source and drain contact structure, comprising:
individual holes etched by an orientation dependent etch from the back of said ISFET to the source and drain regions and terminating at the boundary of said source and drain regions;
regions in the sidewalls of said holes doped to an opposite conductivity type from that of said substrate to provide electrical isolation of the surface of said sidewalls from said substrate; and
a metallized surface deposited on the sidewalls of the holes and extending from the source and drain regions to separate associated contact areas on the back of said ISFET.

13. A method of providing electrical contact to a source region and drain region of an ISFET having a silicon substrate with a crystallographic orientation of (100), comprising the steps of:
providing an etch stopping characteristic in the source and drain regions;
etching with an orientation dependent etch individual holes from the back of the substrate to the source and drain regions to provide access to the source and drain regions, said etch being stopped at the boundary of said source and drain regions by said etch stopping characteristic;

producing an isolation region in the sidewalls of said holes of opposite conductivity type to the substrate; and metallizing over said sidewalls and onto the back to provide the electrical contacts for said source and drain regions on the back of said ISFET.

14. An ISFET pH sensor comprising:

a doped silicon substrate having a (100) crystallographic structure;

a doped source region in the front of said substrate and of conductivity type opposite to said substrate, said source region being doped to have an etch stopping characteristic;

a doped drain region in the front of said substrate and of conductivity type opposite to said substrate, said drain region being doped to have an etch stopping characteristic;

a doped channel stop region in the front of said substrate;

a doped substrate contact region in the back of said substrate;

a gate oxide grown on the front of said substrate;

a field oxide coating on the front surface of said substrate with an opening in the area in front of the gate oxide;

a pH sensitive membrane covering the field oxide coating and the gate region;

individual holes etched from the back of said substrate to the source and drain regions to provide access to the source and drain regions, said etching being done by an orientation dependent etch with the etching terminating at the boundary of the source and drain regions;

a doped region in the sidewalls of said holes of opposite conductivity type to said substrate for electrically isolating said substrate;

a metallized coating covering the surface of said holes and contacting the respective source and drain regions, said coating extending to the back surface of said substrate to form contact pads thereon; and a metallized coating covering the substrate contact region and being in contact therewith.

* * * * *